United States Patent [19]

Komurasaki et al.

[11] Patent Number: 5,384,394
[45] Date of Patent: Jan. 24, 1995

[54] TUMOR CELL GROWTH INHIBITOR

[75] Inventors: Toshi Komurasaki, Kumagaya; Hitoshi Toyoda, Ageo; Daisuke Uchida, Tokyo; Kazunori Hanada, Ageo, all of Japan

[73] Assignee: Taisho Pharmaceutical Co., Ltd., Japan

[21] Appl. No.: 193,778

[22] Filed: Feb. 10, 1994

Related U.S. Application Data

[63] Continuation of Ser. No. 707,012, May 29, 1991, abandoned.

[30] Foreign Application Priority Data

Jun. 6, 1990 [JP] Japan .................................. 2-146143
Feb. 1, 1991 [JP] Japan .................................. 3-011950

[51] Int. Cl.⁶ ................................................ C07K 7/10
[52] U.S. Cl. .................................... 530/324; 435/70.3
[58] Field of Search .................. 530/324; 514/12; 425/70.3

[56] References Cited

U.S. PATENT DOCUMENTS 4,708,948 11/1987 Iwata et al. .............................. 514/2

FOREIGN PATENT DOCUMENTS 8809378 12/1988 WIPO .

OTHER PUBLICATIONS

*Genes and Cancer* (Carney & Sikora ed.)(Wiley & Sons, 1990) pp. 183–189.
Talmadge et al. 13th Int'l Cong. Chemotherapy (Vienna Aug./Sep. 1983) Herbermann et al. ed.) pp. 203/18–203/34.
Patent Abstracts of Japan, vol. 13 No. 408 (Sep. 1989).

*Primary Examiner*—Howard E. Schain
*Attorney, Agent, or Firm*—Lorusso & Loud

[57] ABSTRACT

Novel tumor cell growth inhibitor is a protein which can be obtained from the culture supernatant of 3T3 cell-derived cell line and which has the following properties:

(a) molecular weight 3,700±370 daltons when measured by SDS polyacrylamide gel electrophoresis under reducing and non-reducing conditions;

(b) column property the inhibitor is not substantially adsorbed onto an anionic exchange resin column at pH of about 7.4 but is substantially adsorbed onto a cationic exchange resin column at pH of about 5.0

The inhibitor has an inhibitory activity on human promyelogenic leukemia cells and human uterocervical tumor-derived cells and is useful for the treatment of leaukemia or uterus tumor.

4 Claims, 7 Drawing Sheets

ELUTION PROFILE OF PHENYL 5PW HPLC OF P-1

FIG. 5

PRIMARY STRUCTURE OF P-1

```
  1     2     3     4     5     6     7     8
Val - Gln - Ile - Thr - Lys - Cys - Ser - Ser 9    10    11    12    13    14    15    16
Asp - Met - Asp - Gly - Tyr - Cys - Leu - His 17    18    19    20    21    22    23    24
Gly - Gln - Cys - Ile - Tyr - Leu - Val - Asp 25    26    27    28    29    30    31    32
Met - Arg - Glu - Lys - Phe - Cys - Arg - Cys 33    34    35    36    37    38    39    40
Glu - Val - Gly - Tyr - Thr - Gly - Lys - Arg 41    42    43    44    45    46
Cys - Glu - His - Phe - Phe - Leu
```

FIG. 6

PRIMARY STRUCTURE OF P-2

```
  1     2     3     4     5     6     7     8
Val - Gln - Ile - Thr - Lys - Cys - Ser - Ser 9    10    11    12    13    14    15    16
Asp - Met - Asp - Gly - Tyr - Cys - Leu - His 17    18    19    20    21    22    23    24
Gly - Gln - Cys - Ile - Tyr - Leu - Val - Asp 25    26    27    28    29    30    31    32
Met - Arg - Glu - Lys - Phe - Cys - Arg - Cys 33    34    35    36    37    38    39    40
Glu - Val - Gly - Tyr - Thr - Gly - Lys - Arg 41    42    43    44
Cys - Glu - His - Phe
```

GROWTH INHIBITION EFFECTS
ON HeLa, A-549 AND HL-60 CELLS

GROWTH INHIBITION EFFECTS
ON HeLa, A-549 AND HL-60 CELLS

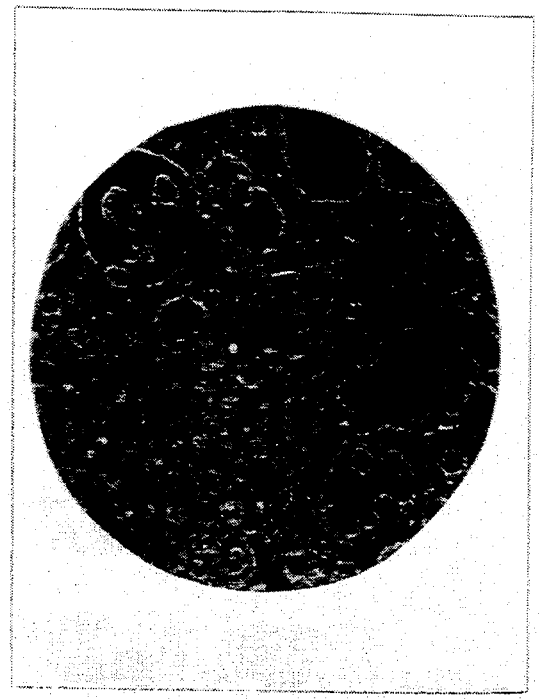
FIG. 9B (P-I)-TREATED CELLS
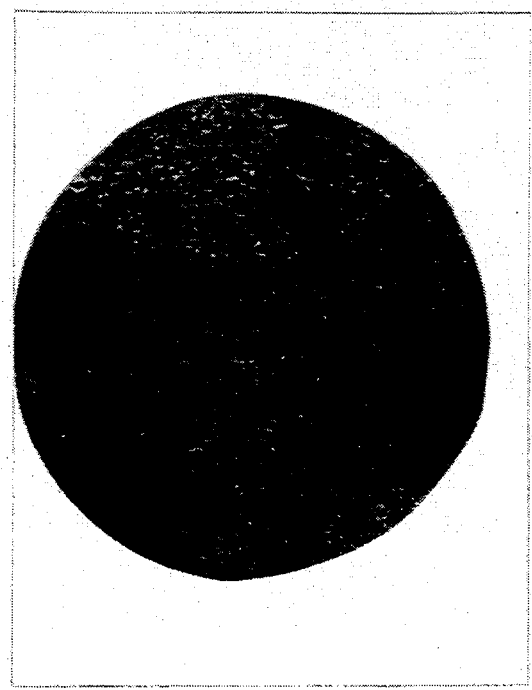
FIG. 9A CONTROL CELLS

TUMOR CELL GROWTH INHIBITOR

This application is a continuation, of application Ser. No. 07/707,012, filed May 29, 1991, now abandoned.

BACKGROUND OF THE INVENTION

1. Field of the Invention

The present invention relates to a novel tumor cell growth inhibitor. More particularly, the present invention relates to a novel tumor cell growth inhibitor which can be obtained from the culture supernatant of 3T3 cell-derived cell line and which exhibits an inhibitory activity on the growth of tumor cells.

2. Related Art Statement

Synthetic drugs such as chemotherapeutic agents and immunotherapeutic agents have been widely used as anti-tumor agents, but involve problems that the specificity is low and that side effects are serious. On the other hand, a variety of tumor cell growth inhibitors have been identified in tissue culture cells. It is considered that these inhibitors could be anti-tumor agents having a high specificity and minimized in side effects. As such substances, there are known, for example, interferon, lymphotoxin and tumor necrosis factor (TNF). Recently, reports have been made on a tumor cytotoxic factor which is obtained from human-derived fibroblast (Japanese Patent Application Laid-Open No. 1-148197), and tumor cell growth inhibitory factor which is obtained from human-derived lung cancer cell (Japanese Patent Application Laid-Open No. 1-187094).

On the other hand, some cell growth inhibitors have been also isolated from fibroblastic cell line 3T3 cells established from cells which had been obtained from Swiss mouse fetus. That is, Natraj et al. have reported that a growth factor is obtained from the surface layer of 3T3 cells in the stationary phase [Proc. Natl. Aca. Sci. USA, 75, 6115–6119 (1978)]. Harel et al. also have reported that a growth inhibitor having a molecular weight of 40 kDa is obtained from the culture supernatant of 3T3 cells [J. Cell. Physiol., 119, 101–106 (1984); ibid., 123, 139–143 (1985)]. However, it is known that these growth inhibitors do not show any significant inhibitory activity on tumor cells.

SUMMARY OF THE INVENTION

Accordingly, an object of the present invention is to provide a novel tumor cell growth inhibitor which has an inhibitory activity on the growth of tumor cells.

According to the present invention, there is provided a tumor cell growth inhibitor which is a protein obtainable from the culture supernatant of 3T3 cell-derived cell line and which has the following properties:

(a) Molecular weight 3,700±370 daltons when measured by SDS polyacrylamide gel electrophoresis under reducing and nonreducing conditions;

(b) Column property

The inhibitor is not substantially adsorbed onto an anionic exchange resin column at pH of about 7.4 but is substantially adsorbed onto a cationic exchange resin column at pH of about 5.0;

(c) Physiological activity

The inhibitor has an inhibitory activity on at least human promyelogenic leukemia cells and human uterocervical tumor-derived cells.

BRIEF DESCRIPTION OF THE DRAWINGS

FIG. 5 shows the primary structure of the tumor cell growth inhibitor (P-1) according to the present invention.

FIG. 6 shows the primary structure of the tumor cell growth inhibitor (P-2) according to the present invention.

FIGS. 9A–B are photographs showing the inhibitory activity of the tumor cell growth inhibitor (P-1) according to the present invention on human uterus cancer cell-derived HeLa cell.

DETAILED DESCRIPTION OF THE INVENTION

Figure 1:
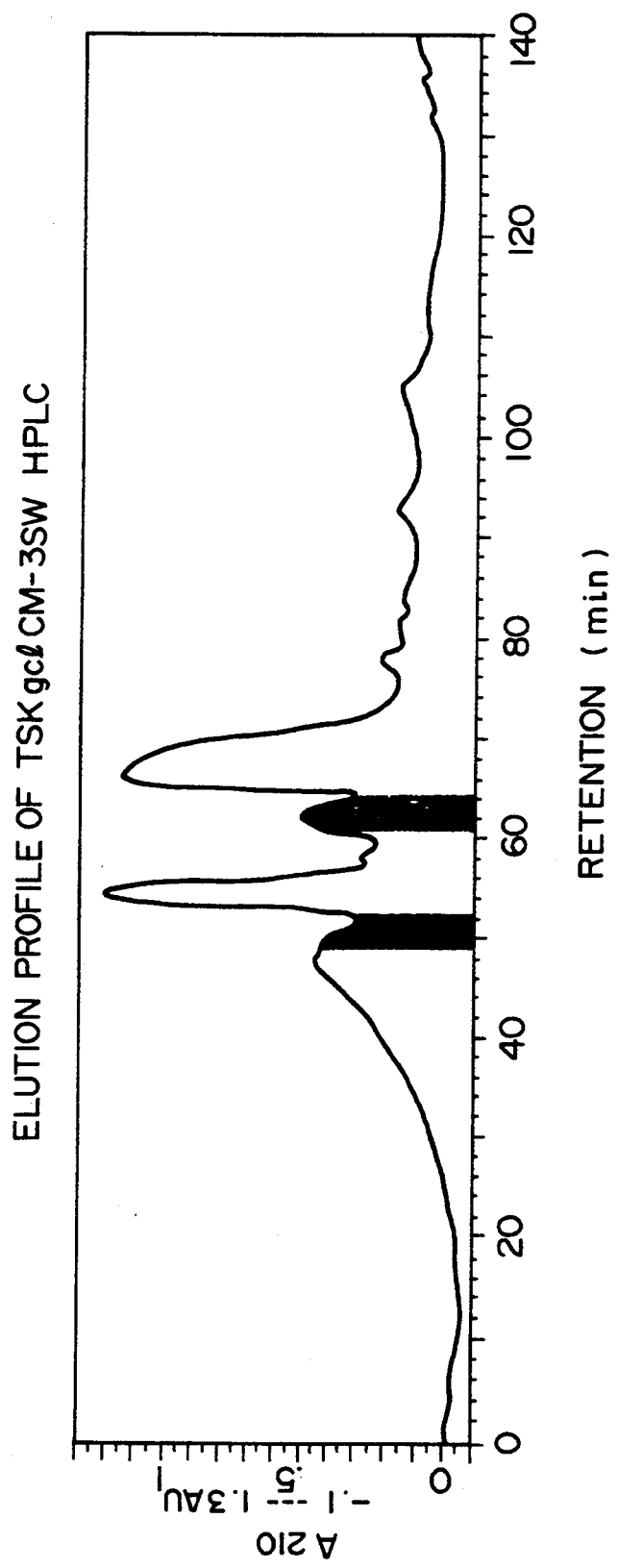
FIG. 1 is a graph showing the elution profile of CM-3SW cationic exchange chromatogram of the tumor cell growth inhibitor according to the present invention.

The tumor cell growth inhibitor of the present invention can be obtained as follows.

Preparation of 3T3 cell-derived cell line

The tumor cell growth inhibitor can be prepared from, e.g., NIH 3T3 cells [J. Virol., 4, 549 (1969)] which is one of fibroblastic cell line 3T3 cells established from cells which are obtained from Swiss mouse fetus. That is, the desired 3T3 cell-derived cell line can be prepared by subculturing, e.g., NIH 3T3 cells in serum-supplemented DF culture medium which is a mixture of Dulbecco's modified MEM [Virology, 8, 396 (1969)] and Ham F-12 [Proc. Natl. Acad, Sci., 53, 288 (1965)], then culturing in DF medium containing hormones such as insulin to isolate or select clones proliferated, further culturing the clones in DF medium alone and selecting clones which can proliferate in DF medium alone.

Preparation of culture supernatant

3T3 cell-derived cell line is initially cultured in DF medium containing serum. When the cells become confluent, the culture medium is removed. After further culturing in serum-free DF medium for a definite period of time, the medium is removed. Then, by culturing in serum-free DF medium, for example, for about 96 to about 120 hours and exchanging the medium with fresh medium every 96 to 120 hours, the culture supernatant is collected. The collected culture supernatant is centrifuged to prepare the culture supernatant.

Purification of tumor cell growth inhibitor

The culture supernatant is subjected to ultrafiltration to perform molecular weight fractionation and concentrate the supernatant. The supernatant is then subjected to salting out and dialysis, if necessary and desired.

Subsequently, an appropriate buffer solution containing the desired component is passed through an anionic exchange resin column such as Q-Sepharose column (Pharmacia) and DEAE-Sepharose (Pharmacia) to partially purify. The tumor cell growth inhibitor of the present invention has a property that the inhibitor is not substantially adsorbed on the anionic exchange resin column. Accordingly, the partially purified inhibitor is obtained by passing through the anionic exchange resin column at pH of about 7.4 and collecting the nonadsorbed fraction.

The inhibitor of the present invention is substantially adsorbed on a cationic exchange resin column at pH of about 5.0. Accordingly, the more purified inhibitor is obtained by passing at pH of about 5.0 through the cationic exchange resin column such as S-Sepharose column (Pharmacia), CM Sepharose column (Pharmacia) and TSK gel CM-3SW (Toyo Soda).

Purification using the anionic and cationic exchange resin columns as described above may also be appropriately performed by changing the order of those purification steps, depending upon necessity.

By subjecting suitably to purification steps such as an adsorption chromatography using hydroxy-appatite column; and high performance liquid chromatography using TSK gel CM-3SW or Phenyl 5PW-RP reversed phase column, the highly purified tumor cell growth inhibitor of the present invention can be obtained.

Properties of tumor cell growth inhibitor

The properties of the tumor cell growth inhibitor of the present invention are described below.

(a) Molecular weight

The inhibitor has a molecular weight of 3,700±370 daltons when measured by SDS polyacrylamide gel electrophoresis under reducing and non-reducing conditions. The inhibitor is a protein having a structure of single strand, because no change is noted in its molecular weight under reducing and non-reducing conditions.

(b) Column property

As described above, the inhibitor has the property that it is not substantially adsorbed onto an anionic exchange resin column at pH of about 7.4 but is substantially adsorbed onto a cationic exchange resin column at pH of about 5.0.

(c) Physiological activity

The inhibitor has an inhibitory activity on at least human promyelogenic leukemia cells such as HL-60, and human uterocervical tumor-derived cells such as HeLa cells. Therefore, the inhibitor of the present invention is useful for the treatment of leaukemia, or solid tumor such as uterus tumor.

(d) Amino acid sequence

The results of amino acids sequencing according to an automatic Edman degradation method using a gaseous phase protein sequencer indicate that the inhibitor has any one of the following two amino acid sequences [(P-1 ] and (P-2)].

(P-1):
```
 1    2    3    4    5    6    7    8    9
Val—Gln—Ile—Thr—Lys—Cys—Ser—Ser—Asp—
 10   11   12   13   14   15   16   17   18
Met—Asp—Gly—Tyr—Cys—Leu—His—Gly—Gln—
 19   20   21   22   23   24   25   26   27
Cys—Ile—Tyr—Leu—Val—Asp—Met—Arg—Glu—
 28   29   30   31   32   33   34   35   36
Lys—Phe—Cys—Arg—Cys—Glu—Val—Gly—Tyr—
 37   38   39   40   41   42   43   44   45
Thr—Gly—Leu—Arg—Cys—Glu—His—Phe—Phe—
 46
Leu
```

(P-2):
```
 1    2    3    4    5    6    7    8    9
Val—Gln—Ile—Thr—Lys—Cys—Ser—Ser—Asp—
 10   11   12   13   14   15   16   17   18
Met—Asp—Gly—Tyr—Cys—Leu—His—Gly—Gln—
 19   20   21   22   23   24   25   26   27
Cys—Ile—Tyr—Leu—Val—Asp—Met—Arg—Glu—
 28   29   30   31   32   33   34   35   36
Lys—Phe—Cys—Arg—Cys—Glu—Val—Gly—Tyr—
 37   38   39   40   41   42   43   44
Thr—Gly—Leu—Arg—Cys—Glu—His—Phe
```

The tumor cell growth inhibitor which is a novel protein can be obtained from the culture supernatant of 3T3 cell-derived cell line. This inhibitor significantly inhibits the growth of human promyelogenic leukemia cells and human uterocervical tumor-derived cells. Therefore, the inhibitor of the present invention is useful for the treatment of leukemia or solid tumors such as uterus cancer.

Hereafter, the present invention is described in more detail by referring to examples.

EXAMPLES

1. Preparation of 3T3 cell-derived cell line

After subculturing NIH 3T3 cells in DF medium (Dulbecco's modified MEM: Ham F-12=1:1) containing 10% fetal bovine serum, the cells were cultured in DF medium containing 5 µg/ml of insulin, 5 µg/ml of transferrin and $2 \times 10^{-8}$ M of a selenate. Clones which grew in the medium were obtained.

Furthermore, a clone which proliferated in DF medium alone was selected from the clones. The clone was subcultured to obtain its cell line. The established cell line was named NIH 3T3 -sf. Culture was carried out at 37° C. in the gaseous phase of 5% $CO_2$. The medium was exchanged by its 70% with fresh medium every 3 other days. Subculture was performed by diluting to 2-fold at the time when the culture cells reached subconfluence. As the medium, a mixture of 50% conditioned medium and 50% fresh medium was prepared and provided for use.

2. Preparation of cell-free culture supernatant of NIH 3T3-sf cells

NIH 3T3-sf cells were cultured in DF medium containing 10% fetal bovine serum. When the cells became confluent, the medium was removed. After washing one with PBS (−), the cells were cultured in DF medium for 48 hours. The medium was removed and culture was continued in fresh DF medium for 96 to 120 hours. The medium was exchanged every 96 to 120 hours and 100 liters of the medium was collected. The collected medium was centrifuged (2000 rpm×10 minutes) to recover the supernatant and stored at −20° C.

3. Purification

1) Q-Sepharose column chromatography

Using pelicon cassette system (ultrafiltration filtering membrane system, fractionated molecular weight of 1000: FUJI FILTER), 100 liters of the recovered culture supernatant was concentrated to about 50-fold. The concentrate was further subjected to salting out with 90% ammonium sulfate saturation followed by centrifugation at 8000 rpm for 60 minutes. The precipitates were dissolved in 20 mM Tris-HCl buffer (pH 7.4) and the solution was dialyzed to the buffer. The dialysate was added to Q-Sepharose column (Pharmacia) (Φ5 cm×5 cm) which has been previously equilibrated with the same buffer to collect the non-adsorbed fraction and the adsorbed fraction.

Conditions for elution were as follows.
Flow rate: 8 ml/min
Fractionation: 2 ml/tube
Eluant: 20 mM Tris-HCl buffer (pH 7.4)

2) S-Sepharose column chromatography

After pH of the non-adsorbed fraction was adjusted to 5.0, the fraction was passed through S-Sepharose column (Pharmacia) (Φ5 cm×6 cm) which has been previously equilibrated with 20 mM acetate buffer (pH 5.0). The active fraction was adsorbed. Thereafter elution was performed with 20 mM Tris-HCl buffer (pH 7.4) to obtain the active fraction.

Conditions for elution were as follows.
Flow rate: 0.85 ml/min
Fractionation: 4 ml/tube
Eluant: 20 mM Tris-HCl buffer (pH 7.4)

3) Hydroxyappatite column chromatography

A pH of the active fraction eluted from the S-Sepharose column was adjusted to 6.0 with acetic acid. The active fraction was loaded onto hydroxyappatite column (Pentax Φ 7.5 cm×10 cm, Asahi Kogaku) which had been previously equilibrated with 20 mM acetate buffer (pH 6.0) to collect the non-adsorbed fraction.

Conditions for elution were as follows.
Flow rate: 1 ml/min
Fractionation: 1 ml/tube
Eluant: 20 mM acetate buffer (pH 6.0)

4) TSK gel CM-3SW column chromatography HPLC

A pH of the active fraction was adjusted to 5.0 with acetic acid. The active fraction was loaded onto TSK gel CM-3SW column (Φ 7.5 cm×7.5 cm, Toso) which had been previously equilibrated with 20 mM acetate buffer (pH 5.0) containing 5% acetonitrile ($CH_3CN$).

Conditions for elution were as follows.
Flow rate: 1 ml/min
Fractionation: 1 ml/tube
Eluant:
A) 20 mM acetate buffer (pH 5.0)/5% $CH_3CN$
B) 20 mM acetate buffer 5.0)/5% $CH_3CN$/0.2 M NaCl
Linear gradient of A—B (120 minutes)

The activity appeared in 2 fractions and eluted with the respective NaCl concentrations of 86 mM (P-1) and 100 mM (P-2) (cf. FIG. 1).

5) Phenyl 5PW-RP reversed phase column chromatography HPLC

Figure 2:
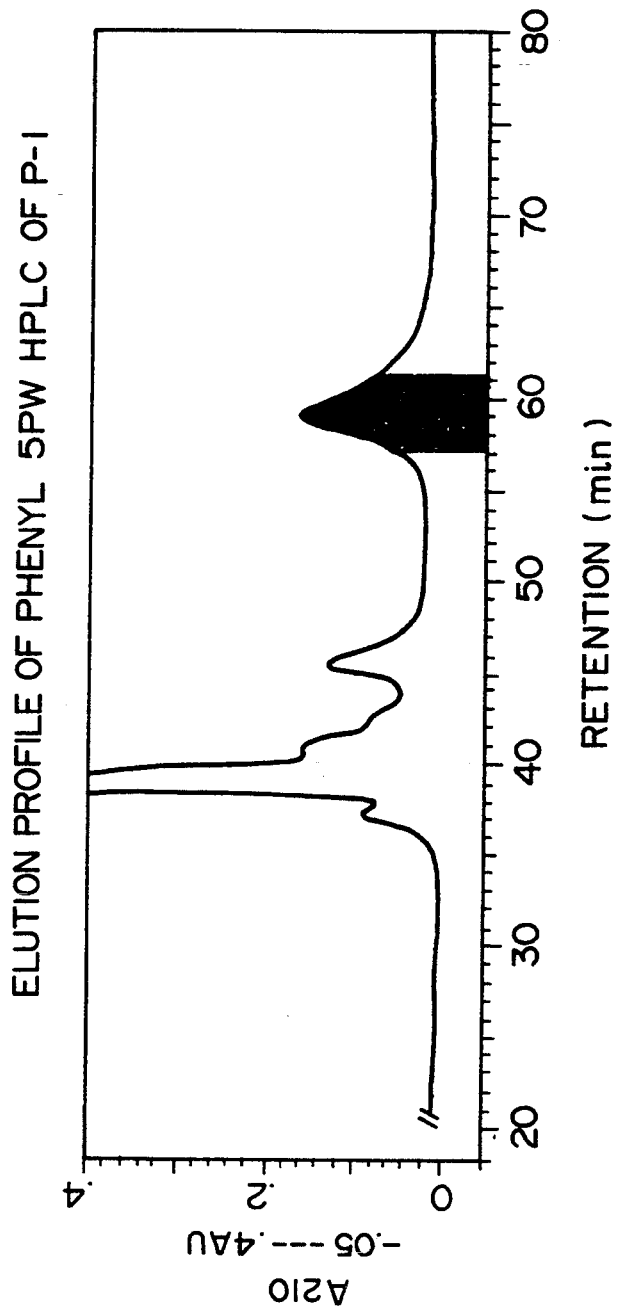
FIG. 2 is a graph showing the elution profile of phenyl 5PW-RP reversed phase HPLC of the tumor cell growth inhibitor according to the present invention.
Figure 3:
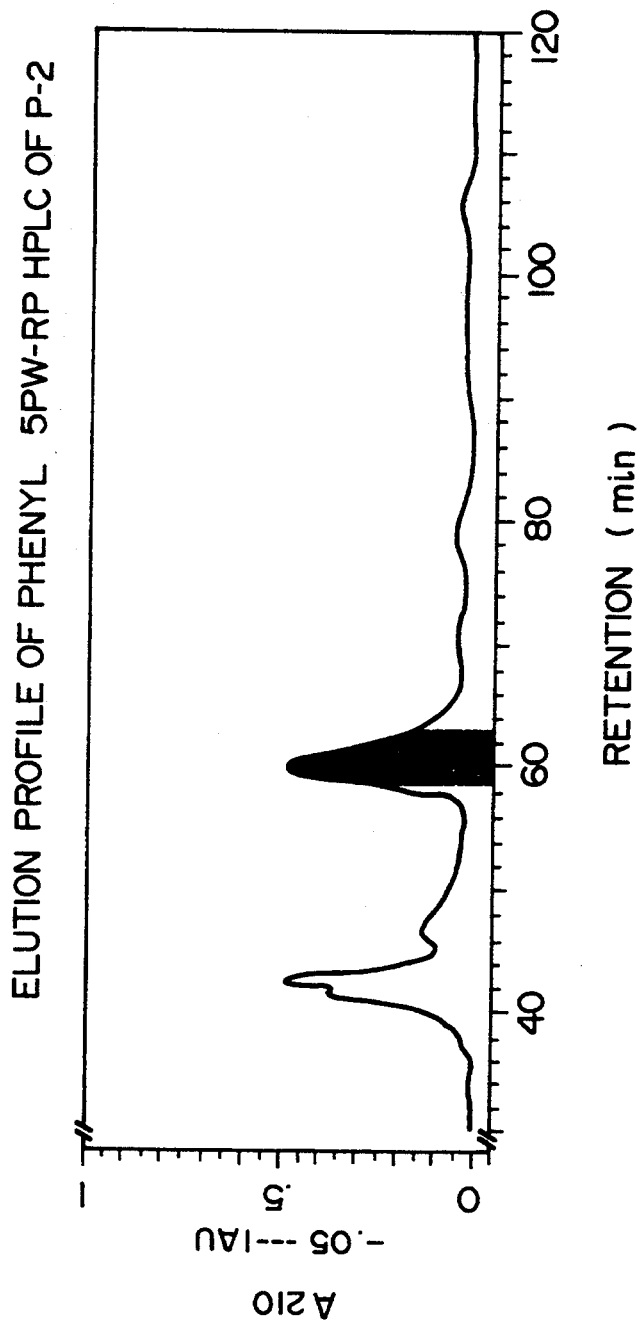
FIG. 3 is a graph showing the elution profile of Phenyl 5PW-RP reversed phase HPLC of the tumor cell growth inhibitor according to the present invention.

The active fraction obtained by CM-3SW HPLC was loaded onto Phenyl 5PW-RP column (Φ4.6 mm×7.5 cm, Toso) which had been previously equilibrated with phosphate buffer (pH 7.4) containing 5% $CH_3CN$. After eluting with 5 mM phosphate buffer (pH 7.4) containing 20% $CH_3CN$ for 20 minutes, elution was further performed under the condition that the elution program was 80 minutes with a linear gradient from phosphate buffer (pH 7.4) in 20% $CH_3CN$ to phosphate buffer (pH 7.4) in 40% $CH_3CN$. Flow rate was 1 ml/min and fractionation was performed in 2 ml/tube. P-1 and P-2 were eluted at the position of 59 to 60 minutes and at the position of 60 to 61 minutes, respectively (cf., FIGS. 2 and 3).

4. SDS-PAGE

Figure 4:
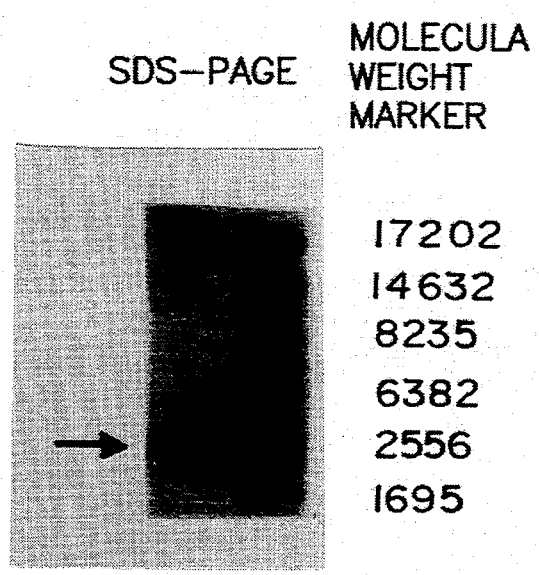
FIG. 4 is a photograph showing the results obtained by subjecting the tumor cell growth inhibitor according to the present invention to SDS-PAGE.

The two active fractions obtained by the reversed phase HPLC were subjected to SDS-PAGE after adding sample buffer (0.0625 M Tris-HCl buffer, p 6.8, 2% SDS, 0.3 M sucrose) to a part of them and heating at 100° C. for 3 minutes. Electrophoresis was performed by a modification of the Laemmli method [Nature, 227, 680 (1970)], using 0.1% SDS-containing 20% polyacrylamide gel (1 mm in thickness). After electrophoresis, protein band was detected by silver staining (silver staining kit, Wako). As a molecular weight marker, there were used myoglobin (17201), myoglobin I+II (14632), myoglobin I (8235), myoglobin II (6383), myoglobin III (2556), and myoglobin 1-14 (1696). As the result, both P-1 and P-2 were detected as a single band at the position of 3,700±370 daltons in molecular weight. No change was noted in the molecular weight under reducing and non-reducing conditions. The results of SDS-PAGE are shown in FIG. 4.

5. Determination of amino acid sequence

With respect to the two purified products, their amino acid sequences were determined by an automatic Edman degradation method using gaseous phase protein sequencer (Model 470A, Applied Biosystems Co., Ltd.). It was revealed that the products had the amino acid sequences as described above (cf. FIGS. 5 and 6).

6. Biological activity

1) Growth inhibition activity on human uterus tumor cells HeLa, human promyelogenic leukemia cells HL-60 and human lung tumor cells A-549

Figure 7:
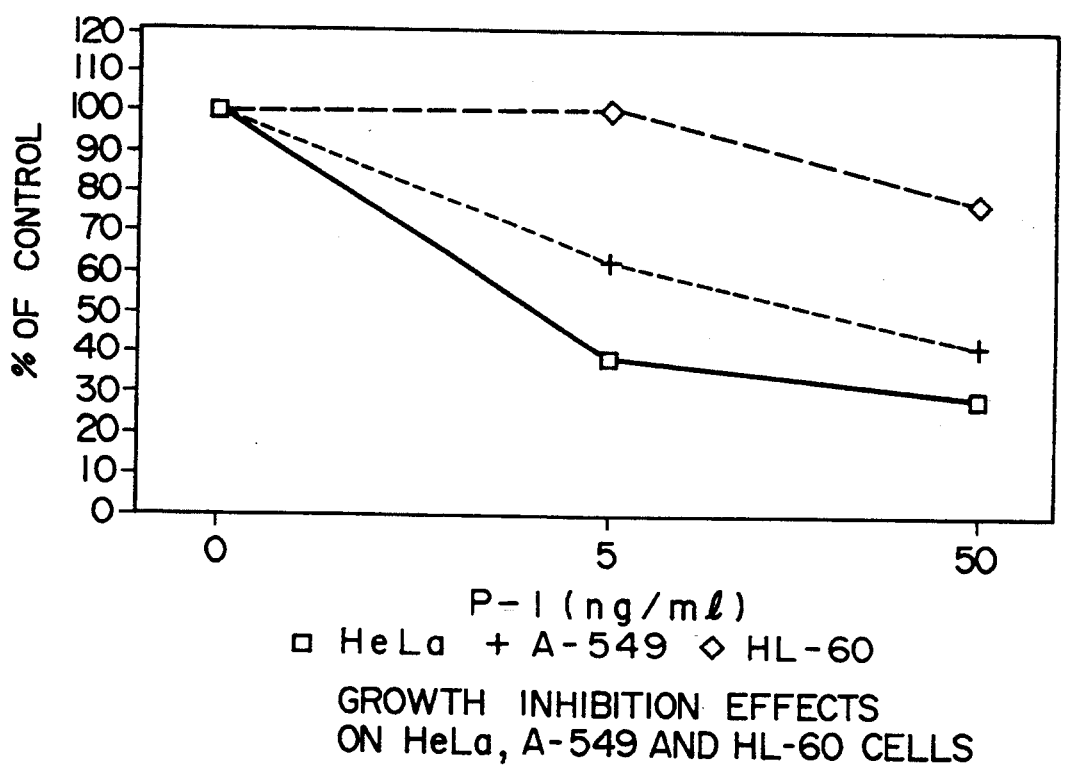
FIG. 7 is a graph showing the growth inhibition. effect of the tumor cell growth inhibitor (P-1) according to the present invention on human uterus cancer cell HeLa, human promyelogenic leukemia cell HL60 and human lung cancer cell A-549.
Figure 8:
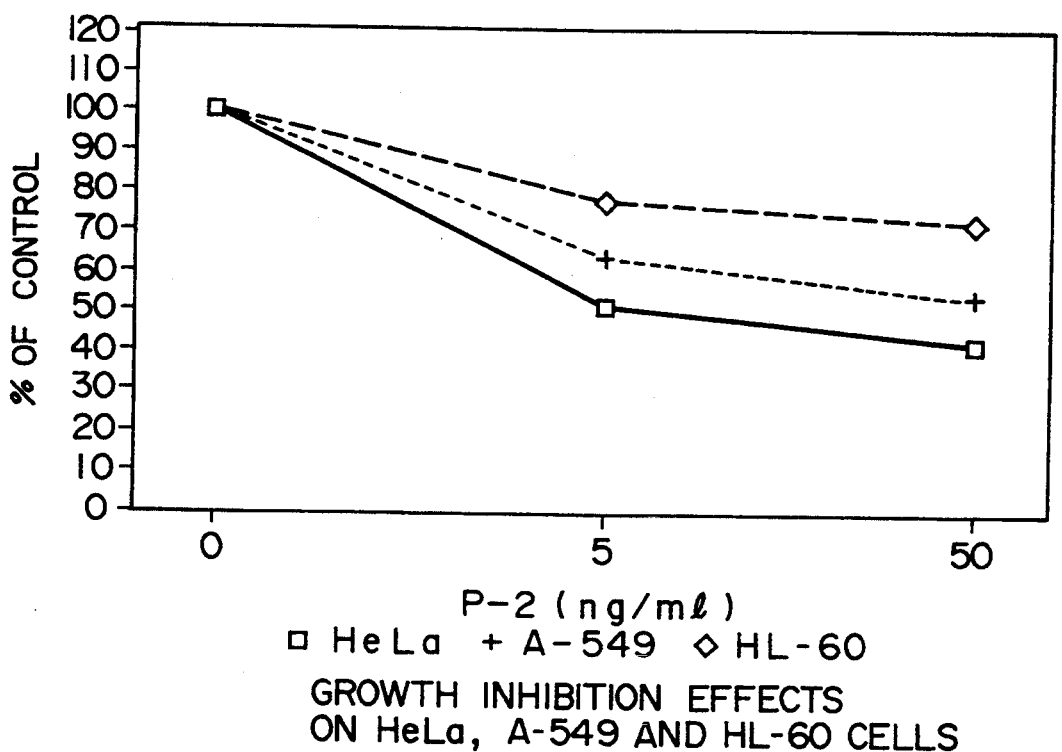
FIG. 8 is a graph showing the growth inhibition effect of the tumor cell growth inhibitor (P-2) according to the present invention on human uterus cancer cell HeLa, human promyelogenic leukemia cell HL-60 and human lung cancer cell A-549.

Each cell was inoculated on a 96 wells plate (Falcon) in $5\times10^3/100$ μl/well followed by culturing at 37° C. for 24 hours in gaseous phase of 5% $CO_2$. The medium was exchanged with a medium containing 5 ng/ml or 50 ng/ml of the purified product [(P-1) or (P-2)] obtained by Phenyl 5PW-RP reversed phase HPLC and the cell was cultured for 6 days. The medium was exchanged every 3 other days. Six days after, living cells was counted by Trypan Blue staining. HL-60 cells were cultured in RDF-2% FBS medium, and HeLa and A-549 cells were cultured in DF-2% FBS medium. The growth inhibition effects on the respective cells are shown in FIGS. 7 and 8. As is evident from FIGS. 7 and 8, the inhibitor of the present invention significantly inhibited growth of Hela cells, A-549 cells and HL-60 cells.

2) The morphological change of human uterus cancer cell-derived HeLa cell

HeLa cells were inoculated on a 48 wells plate (Corning Ltd.) in $5\times10^4$ cells/260 μl of 10% FBS-containing DF/well followed by culturing at 37° C. for 24 hours in gaseous phase of 5% $CO_2$. The each medium was exchanged with a fresh medium containing 10 ng/ml of the purified product (P-1) obtained by Phenyl 5PW-RP reversed phase HPLC, and the cell was further cultured for 48 hours. The morphological change of the cultured cell was observed under a phase contrast microscope. The results were shown in FIGS. 9A—B. FIGS. 9A and 9B show the morphological changes of control cells and (P-1)-treated cells, respectively. As is evident from FIGS. 9A—B, the inhibitor (P-1) of the present invention significantly inhibited growth of HeLa cells.

$3,700 \pm 370$ daltons when measured by SDS polyacrylamide gel electrophoresis under reducing and non-reducing conditions;

(b) column property substantially no amount of the inhibitor is adsorbed onto an anionic exchange resin column at pH of about 7.4 but is adsorbed onto a cationic exchange resin column at pH of about 5.0;

(c) physiological activity the inhibitor has an inhibitory activity on human promyelogenic leukemia cells and human uterocervical tumor-derived cells, and

---

---

What is claimed is:

1. A tumor cell growth inhibitor which is a peptide obtainable from the culture supernatant of 3T3 cell-derived cell line and which has the following properties:

(a) molecular weight said peptide having the following amino acid sequence:

Sequence ID No. 1:
1   2   3   4   5   6   7   8   9   10
Val—Gln—Ile—Thr—Lys—Cys—Ser—Ser—Asp—Met—

-continued 11 12 13 14 15 16 17 18 19 20
Asp—Gly—Tyr—Cys—Leu—His—Gly—Gln—Cys—Ile—

21 22 23 24 25 26 27 28 29 30
Tyr—Leu—Val—Asp—Met—Arg—Glu—Lys—Phe—Cys—

31 32 33 34 35 36 37 38 39 40
Arg—Cys—Glu—Val—Gly—Tyr—Thr—Gly—Leu—Arg—

41 42 43 44 45 46
Cys—Glu—His—Phe—Phe—Leu or

Sequence ID No. 2:
1 2 3 4 5 6 7 8 9 10
Val—Gln—Ile—Thr—Lys—Cys—Ser—Ser—Asp—Met—

11 12 13 14 15 16 17 18 19 20
Asp—Gly—Tyr—Cys—Leu—His—Gly—Gln—Cys—Ile—

21 22 23 24 25 26 27 28 29 30
Tyr—Leu—Val—Asp—Met—Arg—Glu—Lys—Phe—Cys—

31 32 33 34 35 36 37 38 39 40
Arg—Cys—Glu—Val—Gly—Tyr—Thr—Gly—Leu—Arg—

41 42 43 44
Cys—Glu—His—Phe.

2. A peptide for use in inhibiting growth of human promyelogenic leukemia cells or human uterocervical tumor-derived cells, said protein having the following amino acid sequence ID No. 1:

1 2 3 4 5 6 7 8 9 10
Val—Gln—Ile—Thr—Lys—Cys—Ser—Ser—Asp—Met—

11 12 13 14 15 16 17 18 19 20
Asp—Gly—Tyr—Cys—Leu—His—Gly—Gln—Cys—Ile—

21 22 23 24 25 26 27 28 29 30
Tyr—Leu—Val—Asp—Met—Arg—Glu—Lys—Phe—Cys—

31 32 33 34 35 36 37 38 39 40
Arg—Cys—Glu—Val—Gly—Tyr—Thr—Gly—Leu—Arg—

41 42 43 44 45 46
Cys—Glu—His—Phe—Phe—Leu.

3. A peptide for use in inhibiting growth of human promyelogenic leukemia cells or human uterocervical tumor-derived cells said protein having the following amino acid sequence ID No. 2:

1 2 3 4 5 6 7 8 9 10
Val—Gln—Ile—Thr—Lys—Cys—Ser—Ser—Asp—Met—

11 12 13 14 15 16 17 18 19 20
Asp—Gly—Tyr—Cys—Leu—His—Gly—Gln—Cys—Ile—

21 22 23 24 25 26 27 28 29 30
Tyr—Leu—Val—Asp—Met—Arg—Glu—Lys—Phe—Cys—

31 32 33 34 35 36 37 38 39 40
Arg—Cys—Glu—Val—Gly—Tyr—Thr—Gly—Leu—Arg—

41 42 43 44
Cys—Glu—His—Phe.

4. A tumor cell growth inhibitor in accordance with claim 1 having the elution profiles of FIGS. 1–3 and the electrophoresis band of FIG. 4.

* * * * *

UNITED STATES PATENT AND TRADEMARK OFFICE
CERTIFICATE OF CORRECTION

PATENT NO. : 5,384,394
DATED : January 24, 1995
INVENTOR(S) : KOMURASAKI et al

It is certified that error appears in the above-indentified patent and that said Letters Patent is hereby corrected as shown below:

Title Page:
IN THE ABSTRACT:

Last line, delete "leaukemia" and insert --leukemia--.

Col. 2, line 4, "3SW" should read --3-SW--;

line 23, delete the period ".";

line 26, "HL60" should read --HL-60--.

Col. 3, line 57, delete "leaukemia" and insert --leukemia--;

line 64, "[(P-1]" should read --[(P-1)]--.

Col. 4, line 54, delete "days" and insert --day--.

Col. 5, line 61, before "5.0)" insert --(pH--.

UNITED STATES PATENT AND TRADEMARK OFFICE
CERTIFICATE OF CORRECTION

PATENT NO. : 5,384,394
DATED : January 24, 1995
INVENTOR(S) : KOMURASAKI et al

It is certified that error appears in the above-indentified patent and that said Letters Patent is hereby corrected as shown below:

Col. 6, line 19, "p" should read --pH--;
      line 62, "Hela" should read --HeLa--.

Signed and Sealed this

Fifth Day of December, 1995

Attest:

BRUCE LEHMAN

Attesting Officer     Commissioner of Patents and Trademarks

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
    (A) LENGTH: 46 amino acids
    (B) TYPE: amino acid
    (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:1:

Val Gln Ile Thr Lys Cys Ser Ser Asp Met Asp Gly Tyr Cys Leu His
1               5                   10                  15

Gly Gln Cys Ile Tyr Leu Val Asp Met Arg Glu Lys Phe Cys Arg Cys
            20                  25                  30

Glu Val Gly Tyr Thr Gly Leu Arg Cys Glu His Phe Phe Leu
        35                  40                  45

(2) INFORMATION FOR SEQ ID NO:2:

(i) SEQUENCE CHARACTERISTICS:
    (A) LENGTH: 44 amino acids
    (B) TYPE: amino acid
    (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:2:

Val Gln Ile Thr Lys Cys Ser Ser Asp Met Asp Gly Tyr Cys Leu His
1               5                   10                  15

Gly Gln Cys Ile Tyr Leu Val Asp Met Arg Glu Lys Phe Cys Arg Cys
            20                  25                  30

Glu Val Gly Tyr Thr Gly Leu Arg Cys Glu His Phe
        35                  40